US008418551B2

(12) United States Patent
Wunderlich et al.

(10) Patent No.: US 8,418,551 B2
(45) Date of Patent: Apr. 16, 2013

(54) RETRACTABLE ASSEMBLY FOR A SENSOR

(75) Inventors: Ingrid Wunderlich, Radebeul (DE); Thomas Pfauch, Leipzig (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 111 days.

(21) Appl. No.: 13/140,086

(22) PCT Filed: Nov. 27, 2009

(86) PCT No.: PCT/EP2009/065963
§ 371 (c)(1),
(2), (4) Date: Jun. 16, 2011

(87) PCT Pub. No.: WO2010/069736
PCT Pub. Date: Jun. 24, 2010

(65) Prior Publication Data
US 2011/0303006 A1  Dec. 15, 2011

(30) Foreign Application Priority Data

Dec. 18, 2008 (DE) .......................... 10 2008 054 884

(51) Int. Cl.
*G01D 11/24* (2006.01)
(52) U.S. Cl.
USPC ........................................................... 73/431
(58) Field of Classification Search .................... 73/431
See application file for complete search history.

(56) References Cited

U.S. PATENT DOCUMENTS

| 3,559,536 | A | * | 2/1971 | Mason | 91/409 |
| 5,247,872 | A | * | 9/1993 | Hoshi | 92/52 |
| 8,145,400 | B2 | * | 3/2012 | Kusej et al. | 701/68 |
| 2001/0015093 | A1 | * | 8/2001 | Kempe | 73/53.01 |
| 2008/0149465 | A1 | * | 6/2008 | Dragon et al. | 198/836.1 |
| 2008/0255740 | A1 | * | 10/2008 | Kusej et al. | 701/67 |
| 2011/0132618 | A1 | * | 6/2011 | Panian | 166/373 |
| 2011/0303006 | A1 | * | 12/2011 | Wunderlich et al. | 73/431 |

FOREIGN PATENT DOCUMENTS

| DE | 23 28 856 | | 12/1973 |
| DE | 297 20 248 | U1 | 3/1998 |
| DE | 10 2005 051 279 | A1 | 5/2007 |
| DE | 10 2007 035 918 | B3 | 12/2008 |
| EP | 0 372 121 | A1 | 6/1990 |
| EP | 0 551 624 | A1 | 7/1993 |
| EP | 1 104 882 | A2 | 6/2001 |

OTHER PUBLICATIONS

German Search Report.
International Search Report.
English translation of the IPR.

* cited by examiner

*Primary Examiner* — Lisa Caputo
*Assistant Examiner* — Jamel Williams
(74) *Attorney, Agent, or Firm* — Bacon & Thomas, PLLC

(57) ABSTRACT

A retractable assembly for a sensor, which determines a physical and/or chemical, process variable in a process medium. The retractable assembly has a housing, in which a tubular holder for accommodating the sensor is arranged such that it can be moved linearly by a drive unit. At least one cascaded cylinder is provided for the linear shifting of the tubular holder, wherein the cascaded cylinder comprises at least two cylinders arranged one after the other in the direction of the stroke movement. Furthermore, the cascaded cylinder is, or the cascaded cylinders are, embodied and/or operable in such a manner that the sensor is movable into at least two different positions.

13 Claims, 5 Drawing Sheets

RETRACTABLE ASSEMBLY FOR A SENSOR

TECHNICAL FIELD

The invention relates to a retractable assembly for a sensor determining a physical and/or chemical, process variable in a process medium; wherein the retractable assembly has a housing, in which a tubular holder for accommodating the sensor is arranged such that it can be moved linearly by a drive unit. The sensors can be, for example, pH electrodes, amperometric sensors, gas sensors, conductivity sensors, or the like.

BACKGROUND DISCUSSION

Retractable assemblies are widely used in analytical measurements technology. They serve, without process interruption, to withdraw sensors from the process, even in the case of high process pressures, and then to reintroduce the sensors back into the process. For this, the sensor is automatically or manually moved back and forth between a measuring position and a maintenance, or service, position. In the maintenance position, the sensor is checked, calibrated, replaced or just simply cleaned, which occurs in a wash/rinse/calibration chamber, and depending on the application, is of great importance for the quality of the measurements. The process variable to be determined or monitored is ascertained in the measuring position. Used as a drive unit is usually a pneumatic cylinder, which is arranged concentrically around the tubular holder or the immersion tube. The drive unit and wash/rinse/calibration chamber are, in most cases, so arranged that process medium can reach the drive unit in the case of malfunction or leakage.

Two different solutions are used for preventing process medium from getting into the retractable assembly: In a first form of embodiment, a ball valve, or a plug valve is used, which via a rotating, e.g. spherical element opens or closes the opening through which the sensor is moved into and out from the process. In a second form of embodiment, a closing plug is used. This closing plug is an integral component of the retractable assembly.

Ball valve assemblies are preferably applied in media with a solids fraction. Solids are understood to be fibers, as well as clinging, baked-on lime and similar materials. In ball valve assemblies, the sensor is conveyed into and out of the process out in isolation from the closing/opening mechanism. For this, the ball valve is closed or opened. For the purpose of cleaning the sensor, the sensor is brought into the maintenance position in a rinsing chamber separated from the process.

Retractable assemblies are available and sold by the assignee in different embodiments under the name 'Clean-Fit'. For example, an assembly with a closing plug is CleanFit S, CPA 471-474. In these retractable assemblies, the holder for the sensor is itself embodied as a sealing element. The front part of the holder is embodied as a plug, which already radially seals off the process during the retraction. The construction of the sealing system of the assemblies CPA 471 and CPA 472 assures, in such a case, a perfect isolation between the rinsing chamber, and, therefore, the 'environment', and the process, and, indeed, in every position of the sensor holder.

Relatively complex open loop control, or closed loop control solutions are used for the purpose of detecting the correct assuming of the measuring or service position. In order to monitor the correct positioning of the tubular holder or immersion tube, end position switches are usually utilized. In general it can be said that only two positions are implementable with the known solutions without an overly large technical effort. The assuming of a third position, in which comprehensive cleaning and washing or rinsing concepts of all components contacting the medium can be taken into consideration, for example, leads to a technically complex solution.

The known solutions are not quite problem free in that there is no reliable spatial isolation of the wash/rinse/calibration chamber, the immersion tube and the assembly drive. As a result, in the case of an unnoticed leak in the region of the rinsing chamber, process medium can reach the drive unit, which can lead to a failure of the drive unit; moreover, it is possible that the process medium can reach the environment via the drive unit.

In order to assure that the sensor is always arranged in a defined position in relation to the immersion tube and therewith the process, a separate twist preventer is provided in the known solutions. This is usually externally built on and causes an increased functional risk as well as extra costs.

SUMMARY OF THE INVENTION

An object of the invention is to provide a structurally simply embodied, retractable assembly allowing a sensor to assume different positions.

The object is achieved by providing at least one cascaded cylinder for the linear shifting of the tubular holder, wherein the cascaded cylinder comprises at least two—thus two, three or more—cylinders arranged one after the other in the direction of the stroke movement; and that the cascaded cylinder/the cascaded cylinders is/are embodied and/or operable in such a manner that the sensor is movable into at least two different positions. A synonym for a cascaded cylinder is a multi-position cylinder. The tubular holder for the sensor is also referred to as an immersion tube or as a tubular, sensor holder. More than two positions can be defined with a cascaded cylinder, or with cascaded cylinders, having two or more cylinders, without great technical effort. Of course, the number of cylinders arranged one after the other can also be greater than two. The defined assuming of more than two positions enables an easy and/or individual washing or rinsing concept, in which all components contacting the medium, including the sealing surfaces, can be cleaned. This is explored in greater detail later.

In an embodiment, the cascaded cylinder is, or the cascaded cylinders are, arranged concentrically to the longitudinal axis of the tubular holder. In such case, the tubular holder performs the function of the piston.

However, it is especially advantageous, in connection with the retractable assembly of the invention, when more than one cascaded cylinder is provided. The cascaded cylinders are then preferably arranged axially symmetrically to the longitudinal axis of the tubular holder. A preferred embodiment of the retractable assembly of the invention provides that, in the case of two cascaded cylinders, these are arranged diametrally on opposite sides of the tubular holder, wherein the longitudinal axes of the two cascaded cylinders and the longitudinal axis of the tubular holder are oriented parallel to one another.

Alternatively, a cascaded cylinder is provided, which is arranged laterally to the tubular holder, wherein the longitudinal axis of the cascaded cylinder and the longitudinal axis of the tubular holder are oriented parallel to one another.

If the cascaded cylinder is arranged concentrically with the tubular holder, then, just as in the state of the art, a separate externally built on, twist preventer must be provided for the defined positioning of the sensor relative to the process. If the cascaded cylinder is, or the cascaded cylinders are, provided laterally to the tubular holder, then they are, in each case, secured to the tubular holder via a coupling element. In this way, an intrinsic twist preventer in each defined assumeable position of the tubular holder is implemented. Moreover, this arrangement assures a meaningful spatial isolation of the drive unit, on the one hand, and the media contacting, functional group, formed by the tubular holder and the wash/rinse/calibration chamber, on the other hand. This isolation, as already mentioned above is very advantageous, both as regards safety as well as also functional aspects.

A preferred further development of the retractable assembly of the invention provides that the drive unit and/or the cascaded cylinder/the cascaded cylinders is/are so embodied that the sensor is movable to a measuring position, a first service position and a second service position.

Preferably, but in no way limiting, the second service position lies between the measuring position and the first service position. The sensor enters the process medium in the measuring position and determines or monitors the process variable. The sensor is isolated from the process medium in the first service position, e.g. via one of the options named in the description in the introduction, and can be cleaned, calibrated or replaced in this position. At least one seal, which seals the sensor from the process medium in the first service position, can be cleaned in the second service position. Likewise, this second service position is distinguished in that all components of the tubular holder coming in contact with the medium can be cleaned here. Therefore, this arrangement with the second service position is especially designed for processes with high hygienic requirements.

Preferably, the drive unit is embodied as a pneumatic control. In this connection, it is provided that the pneumatic control supplies a higher pressure to the first cylinder of the cascaded cylinder, which faces the process medium, than to the second cylinder, which faces away from process medium, for the assuming of the second service position. The pressure difference is so dimensioned that the desired, defined, second service position is brought about.

Alternatively, it is provided that a pressure reducer is interposed before one of the cylinders, e.g. the cylinder facing away from the process medium. The pressure reducer is so embodied that the difference between the pressures of both cylinders, in the case of equal pressure supply from the pneumatic drive unit, is so dimensioned that the second service position is automatically assumed.

Another variant provides that, in each case, one of the two cylinders of the cascaded cylinder/cylinders has smaller dimensions than the other cylinder, wherein the difference in the dimensions is so selected that different forces reign with equal pressure supply to both cylinders and that the second service position is assumed with certainty due to the structural conditions. In this way, the assuming of at least one additional position can be implemented without problem.

In principle, all of the solutions named above permit the different defined positions to be assumed without the use of limit switches. Nevertheless, at least one end position switch can be associated with each of the different positions.

An advantageous embodiment of the retractable assembly of the invention provides that the seals are elastomeric seals or hard sealing elements.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1:
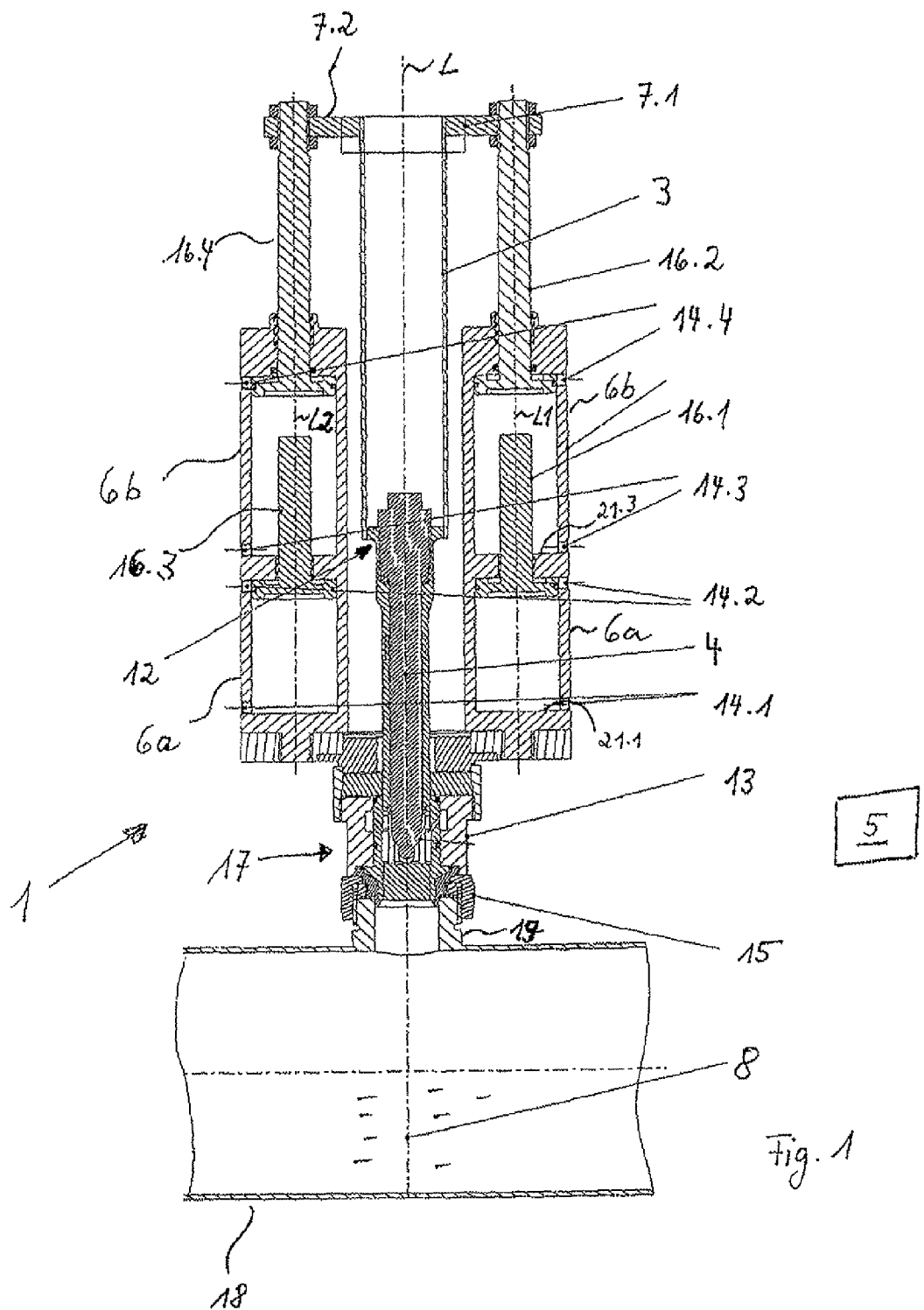
FIG. 1 is a longitudinal section through an embodiment of the retractable assembly of the invention in the first service position.
Figure 2:
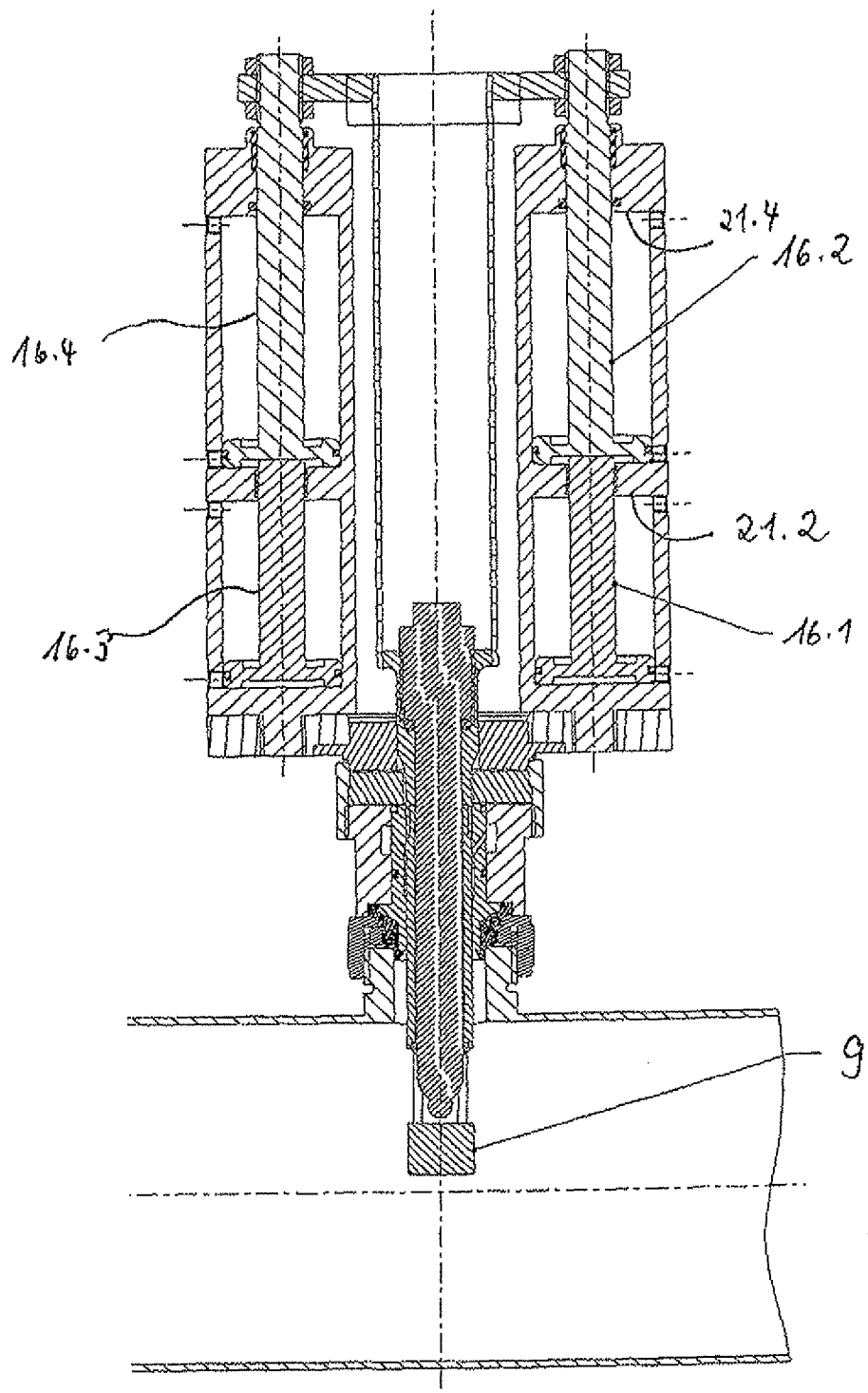
FIG. 2 is a longitudinal section through the retractable assembly of FIG. 1 in the measuring position.
Figure 3:
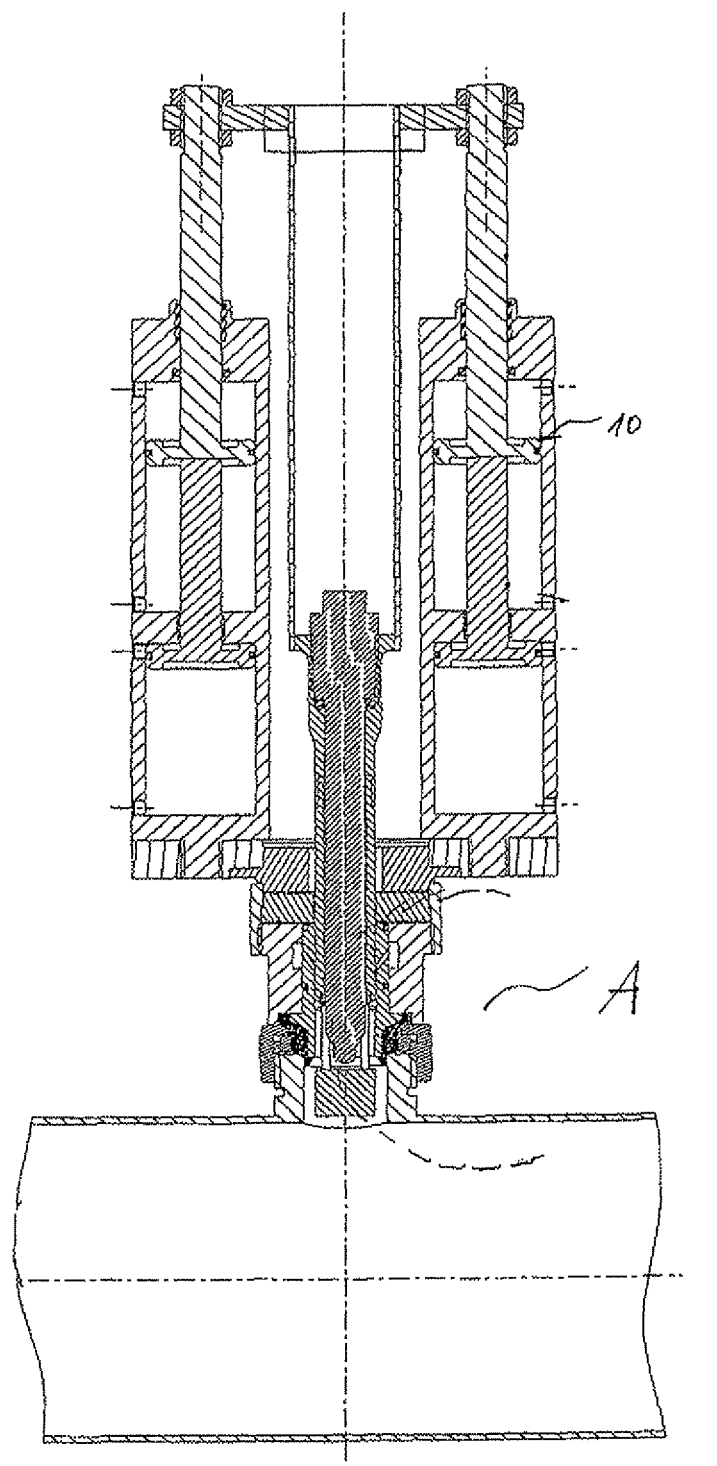
FIG. 3 is a longitudinal section through the retractable assembly of FIG. 1 in the second service position.

FIGS. 1, 2 and 3 show, in each case, in longitudinal section, different positions of an embodiment of the retractable assembly 1 of the invention: FIG. 2 shows the case wherein the retractable assembly 1 is located in the measuring position and the sensor 4 is in contact with the process medium 8 for determining or monitoring a process variable of the process medium 8. FIG. 1 shows the case wherein the retractable assembly 1 is located in the first service position SP1. In service position SP1, the sensor 4 can be cleaned, calibrated or replaced. FIG. 3 shows the retractable assembly 1 in the second service position SP2: In this position SP2, it is possible to clean all functional groups of the tubular holder 3 coming in contact with the process medium 8, so that also highest hygiene requirements can be satisfied. Especially, in the second service position, the seals 9, and the corresponding sealing surfaces 20, which are located between the second service position SP2 and the process, are cleaned, Furthermore, the retractable assembly 1 of the invention enables assuming the defined positions MP, SP1, SP2 in any sequence, depending on need. A very simple construction for assuming the different positions provides that e.g. the cylinder 6a facing the process medium 8 is shorter than the cylinder 6b facing away from the process medium 8.

With the retractable assembly 1 shown, the three positions MP, SP1, SP2 are selectable by the drive unit 5 without requiring an end position switch or other position detectors to be applied. However these can be applied optionally and for redundancy purposes.

The invention is described in detail based on FIG. 1 in the following. The reference characters in FIG. 2 and FIG. 3 have been largely omitted, since the reference characters there are identical to those in FIG. 1. The retractable assembly 1 is secured via a process connection 17 with the union nut 15 to the nozzle 19 of a tubular container 18. The tubular holder 3, in whose sensor receptacle 12 the sensor 4 is secured, is arranged in a housing 2 (not separately illustrated in FIG. 1) of the retractable assembly.

Peripherally to the tubular holder 3, two equally constructed, cascaded cylinders 6.1, 6.2 are diametrally arranged relative to one another. Each of the two cascaded cylinders 6.1, 6.2 comprises two cylinders 6a, 6b, wherein the cylinder 6a faces the process medium 8 and cylinder 6b faces away from the process medium 8. Pistons 16.1, 16.2 are associated with the cylinders 6a, 6b. In the illustrated case, the cascaded cylinders 6.1, 6.2 are arranged symmetrically to the longitudinal axis L of the tubular holder 3. Of course, the arrangement can also be asymmetrical. In principle, any arrangement of cascaded cylinders 6 can be used in connection with the retractable assembly 1 of the invention. The same can be said regarding the number of cylinders 6a, 6b, one connected after the other in series, of a cascaded cylinder 6.1, 6.2. The more cylinders that are arranged in series one after the other, the more positions can be defined in a simple manner.

Cylinders 6a, 6b are supplied with pressurized air from the pneumatic control 5 via the pneumatic connections 14.1, 14.2, 14.3, 14.4 associated with the individual cylinders 6a, 6b, so that, in each case, the desired position is brought about.

In order to assume the first service position SP1 shown in FIG. 1, the cylinders 6a, 6b are supplied with pressurized air via the pneumatic connections 14.1 and 14.3. In this way, the pistons 16.1 of the cylinder 6a and the pistons 16.2 of the cylinder 6b are each driven against the upper stops 21.2, 21.4. End position switches, which signal the reaching of the end position, are thus not required, but can, however, be provided at the corresponding locations for purposes of redundancy.

In order to assume the measuring position MP shown in FIG. 2, the cylinders 6a, 6b are supplied with pressurized air via the pneumatic connections 14.2 and 14.4. In this way, the pistons 16.1 of the cylinders 6a and the pistons 16.2 of the cylinders 6b are each driven against the lower stops 21.1, 21.3. Thus, end position switches are also not required here.

In order to assume the second service position SP2, the cylinders 6a facing the process medium 8 are supplied with pressurized air via the process connections 21.1, so that the pistons 16.1 press against the upper stops 21.1 of the cylinder 6a. Since the cylinders 6b facing away from the process medium 8 are longer than the cylinders 6a facing the process medium 8, the pistons 16.2 of the cylinders 6b facing away from the process medium 8 come to rest in the intermediate position shown in FIG. 3. An end position switch for the service position SP2 can be optionally mounted in the intermediate position.

Additionally, or alternatively, to the solution described earlier, the retractable assembly can also be moved into the service position SP2, when care is taken that the cylinder 6a facing the process medium 8 is supplied with a higher pressure than the cylinder 6b facing away from the process medium 8. This can be achieved in a simple manner, for example, by placing a pressure reducer 10 in front of each of the pneumatic connections 14.3 of the cylinders 6b facing away from the process medium 8. Alternatively to the pressure reducer 10, the cylinders 6a facing the process medium 8 can be designed to be greater in cross section than the cylinders 6b facing away from the process medium 8.

Alternatively to the above described example, the second service position SP2 can also be located above the first service position SP1 or below the measuring position MP. For this, the cascaded cylinders 6.1, 6.2 must be correspondingly adapted in their dimensioning and/or connections.

The advantages of the earlier described arrangement compared to the arrangements known from the state of the art are listed again as follows:

Two or more positions of the retractable assembly 1 are assumeable in a defined manner without requiring an end position switch or other position detectors.

Figure 3A:
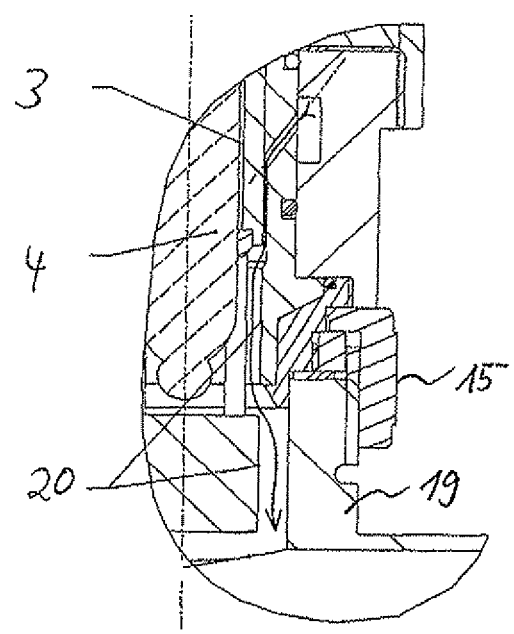
FIG. 3a is a detail drawing of the portion A of FIG. 3.

Cleaning concepts, especially hygienic washing or rinsing concepts, for all components of the retractable assembly 1 that contact the medium are able to be implemented in more than two positions. In the case illustrated, the sealing surfaces 20 between the measuring position MP and the first service position SP1 are cleaned in the service position 2 (see also FIG. 3a for this).

Selective use of the additional position, or additional positions, is possible.

Through eccentric arrangement of the cascaded cylinders 6, or the cascaded cylinders 6.1, 6.2, twist prevention is intrinsically included for the tubular holder 3.

The pneumatic control 5 and the regions of the retractable assembly 1 contacting the medium, the wash/rinse/calibration chamber 13 and the tubular holder 3, are spatially isolated from one another, which enables detection of leakages in the washing or rinsing chamber region.

Moreover, a leakage does not unavoidably lead to damage to or destruction of the pneumatic drive unit 5.

Depending on the embodiment selected, standardized pneumatic cylinders in the form of purchased parts can be used.

Figure 4:
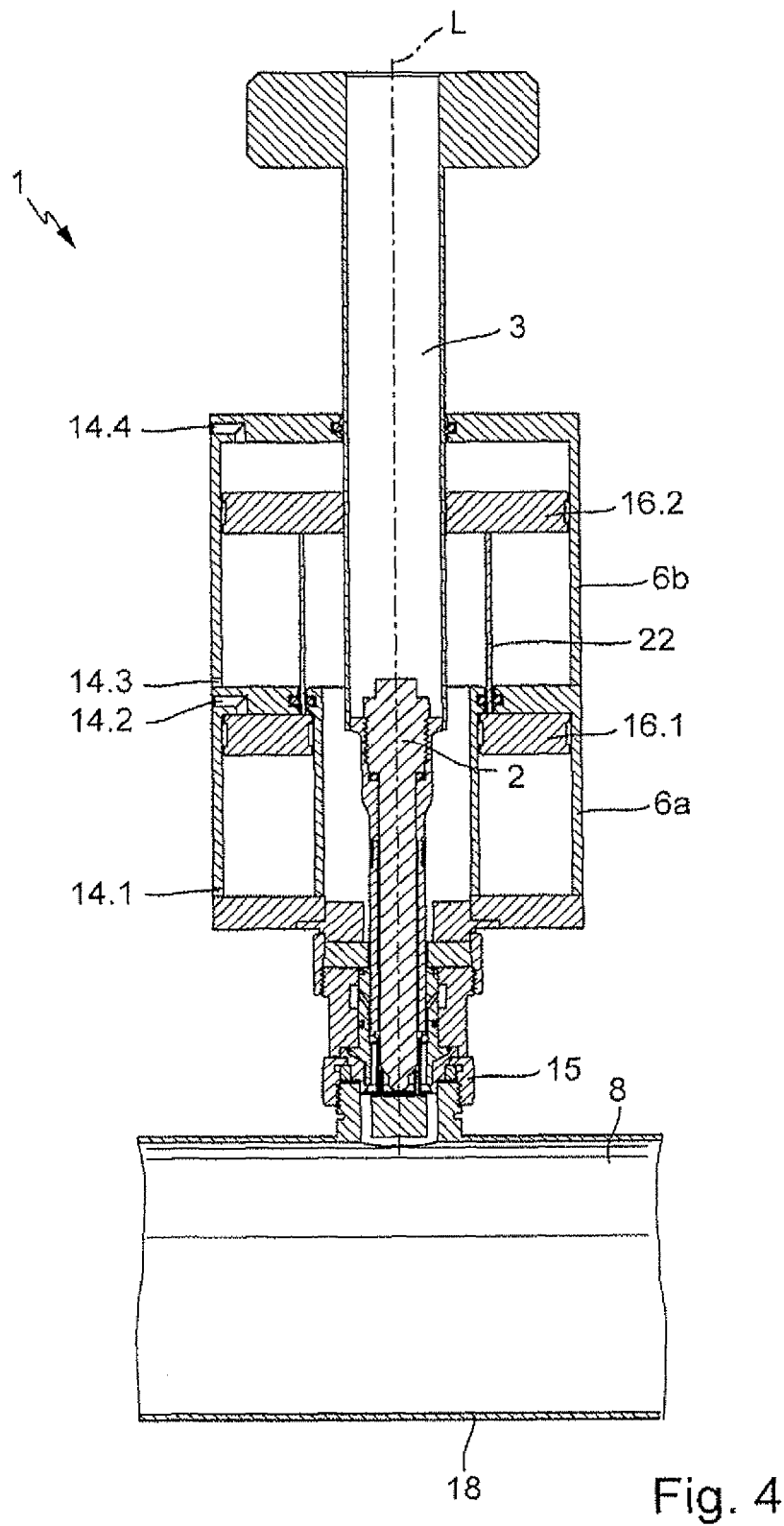
FIG. 4 is a longitudinal section through a second form of embodiment having cascaded cylinders arranged rotationally symmetrically to the longitudinal axis of the retractable assembly.

FIG. 4 shows a longitudinal section through a second form of embodiment with cascaded cylinders 6a, 6b arranged rotationally symmetric to the longitudinal axis L of the retractable assembly 1. The retractable assembly is in the first service position SP1. The cascaded cylinders 6.1, 6.2 are arranged rotationally symmetrically around the tubular holder 3 and, respectively, around the immersion tube with the sensor receptacle. While the piston 16.2 is directly coupled with the immersion tube 3 as piston rod, the piston rod 22 of the piston 16.1 is in the form of a pipe. As is the case in the forms of embodiment described in FIGS. 1 to 3, the particular position SP1, MP, SP2, of the sensor 2 is controlled via a corresponding pressurizing of the pneumatic connections 14.1, 14.2, 14.3, 14.4. Control occurs via a drive unit (not separately shown in FIG. 4).

The invention claimed is:

1. A retractable assembly for a sensor determining a physical and/or chemical, process variable in a process medium, comprising:
   a tubular holder;
   a drive unit;
   a housing, in which said tubular holder for accommodating the sensor is arranged such that it can be moved linearly by said drive unit;
   at least one cascaded cylinder is provided for the linear shifting of said tubular holder, said at least one cascaded cylinder comprises at least two cylinders arranged one after the other in the direction of the stroke movement, wherein:
   said cascaded cylinder or the cascaded cylinders is/are embodied and/or operable in such a manner that the sensor is movable into at least two different positions.

2. The retractable assembly as claimed in claim 1, wherein:
   said cascaded cylinder or said cascaded cylinders is/are arranged concentrically to the longitudinal axis of said tubular holder.

3. The retractable assembly as claimed in claim 1, wherein:
   said cascaded cylinder or said cascaded cylinders is/are arranged axially symmetrically to the longitudinal axis of said tubular holder.

4. The retractable assembly as claimed in claim 1, wherein:
   said cascaded cylinder is arranged laterally to said tubular holder; and
   the longitudinal axis of said cascaded cylinder and the longitudinal axis of said tubular holder are oriented parallel to one another.

5. The retractable assembly as claimed in claim 1, wherein:
   two cascaded cylinders are provided, which are arranged on diametrally opposite side regions of said tubular holder; and
   the longitudinal axes of both said cascaded cylinders and the longitudinal axis of said tubular holder are oriented parallel to one another.

6. The retractable assembly as claimed in claim 1, further comprising:

at least one coupling element, via which a cascaded cylinder or each of a number of cascaded cylinders is rigidly connected with said tubular holder.

7. The retractable assembly as claimed in claim 1, wherein:
said drive unit and/or said cascaded cylinder or the cascaded cylinders are/is so embodied that the sensor is movable to a measuring position, a first service position and a second service position.

8. The retractable assembly as claimed in claim 7, wherein:
for the case, in which the second service position lies between the measuring position and the first service position, the sensor is in the process medium in the measuring position and determines the process variable there;
the sensor is isolated from the process medium and is cleanable, able to be calibrated or exchangeable in the first service position; and
at least one seal, which seals the sensor in the first service position from the process medium, is cleanable in the second service position.

9. The retractable assembly as claimed in claim 1, wherein:
said drive unit is embodied as a pneumatic control; said pneumatic control, in order to cause the sensor to assume the second service position, supplies said first cylinder, which faces the process medium of said cascaded cylinder with a higher pressure than said second cylinder, which faces away from the process medium.

10. The retractable assembly as claimed in claim 1, wherein:
for the case, in which said drive unit is embodied as a pneumatic control, a pressure reducer is placed in front of one of said cylinders of said cascaded cylinder; and
said pressure reducer is so embodied that the difference in pressure, in the case of equal pressure supply by said pneumatic drive unit, is so sized that the second service position is assumed.

11. The retractable assembly as claimed in claim 1, wherein:
in each case, one of said two cylinders of said cascaded cylinder or said cascaded cylinders has smaller dimensions than the other cylinder; and
the difference in dimensions is so selected that different forces reign in the case of equal pressure supply to both cylinders and the second service position is assumed.

12. The retractable assembly as claimed in claim 1, further comprising:
at least one end position switch associated with each of the different positions.

13. The retractable assembly as claimed in claim 8, wherein:
said seal is a hard sealing element, which is preferably manufactured of ceramic; or
said seal is an elastomeric seal.

* * * * *